United States Patent
Baxter et al.

(10) Patent No.: US 8,858,502 B2
(45) Date of Patent: Oct. 14, 2014

(54) SYSTEMS AND METHODS FOR EXTERNAL PRESSURE SENSING

(71) Applicant: Alcon Research, Ltd., Forth Worth, TX (US)

(72) Inventors: Vincent A. Baxter, Temecula, CA (US); Raphael Gordon, Ladera Ranch, CA (US); Gregory S. Layser, Oceanside, CA (US); Sean Christopher Madden, Mission Viejo, CA (US); Gary P. Sorensen, Laguna Niguel, CA (US); Daniel J. Wilson, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/648,330

(22) Filed: Oct. 10, 2012

(65) Prior Publication Data
US 2014/0100518 A1    Apr. 10, 2014

(51) Int. Cl.
*A61M 1/00* (2006.01)
*A61M 31/00* (2006.01)
*G01L 9/12* (2006.01)
*A61M 3/02* (2006.01)

(52) U.S. Cl.
CPC ............ *A61M 3/0233* (2013.01); *G01L 9/12* (2013.01)
USPC .............................. 604/153; 604/67; 604/131

(58) Field of Classification Search
USPC ........... 604/65, 67, 131, 132, 141, 153, 890.1
See application file for complete search history.

(56) References Cited

U.S. PATENT DOCUMENTS

| | | | |
|---|---|---|---|
| 5,399,166 A * | 3/1995 | Laing | 604/146 |
| 5,423,759 A * | 6/1995 | Campbell | 604/153 |
| 5,733,256 A | 3/1998 | Costin | |
| 7,736,335 B2 * | 6/2010 | Radgowski et al. | 604/153 |
| 7,806,865 B1 | 10/2010 | Wilson | |
| 2008/0114372 A1 | 5/2008 | Edwards et al. | |
| 2011/0046558 A1 | 2/2011 | Gravesen et al. | |

OTHER PUBLICATIONS

International Searching Authority, International Search Report, PCT/US2013/063228, Mar. 6, 2014, 2 pages.
International Searching Authority, Written Opinion of the International Searching Authority, PCT/US2013/063228, Date of WO, 5 pages, Mar. 6, 2014.

* cited by examiner

*Primary Examiner* — Nathan R Price

(57) ABSTRACT

In various embodiments, a device for delivering pressurized irrigation may include a squeeze plate and a pressure sensor module. The squeeze plate may move relative to the pressure sensor module to apply pressure to a flexible container (e.g., a bag of irrigation fluid) between the squeeze plate and the pressure sensor module. The pressure sensor module may include a pressure sensor to measure a force exerted on the pressure sensor module by the flexible container as pressure is applied to the flexible container from the squeeze plate. In some embodiments, the pressure sensor module may include a bag contact plate and the pressure sensor may measure a force exerted on the bag contact plate by the flexible container located between the bag contact plate and the squeeze plate. In some embodiments, the pressure sensor may sense a pressure associated with the flexible container without an intervening bag contact plate.

14 Claims, 10 Drawing Sheets

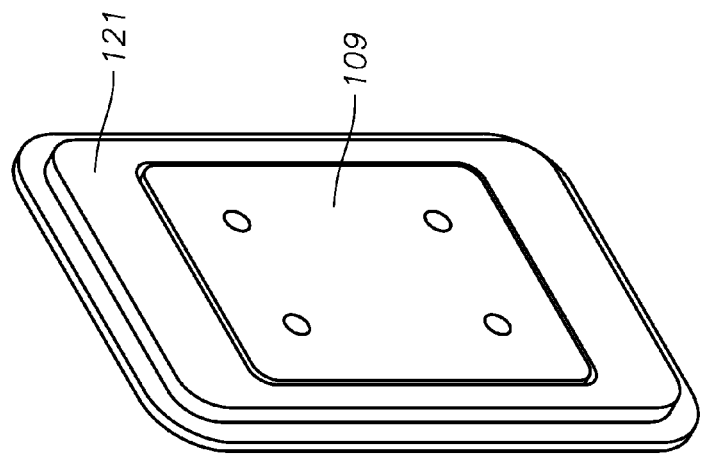
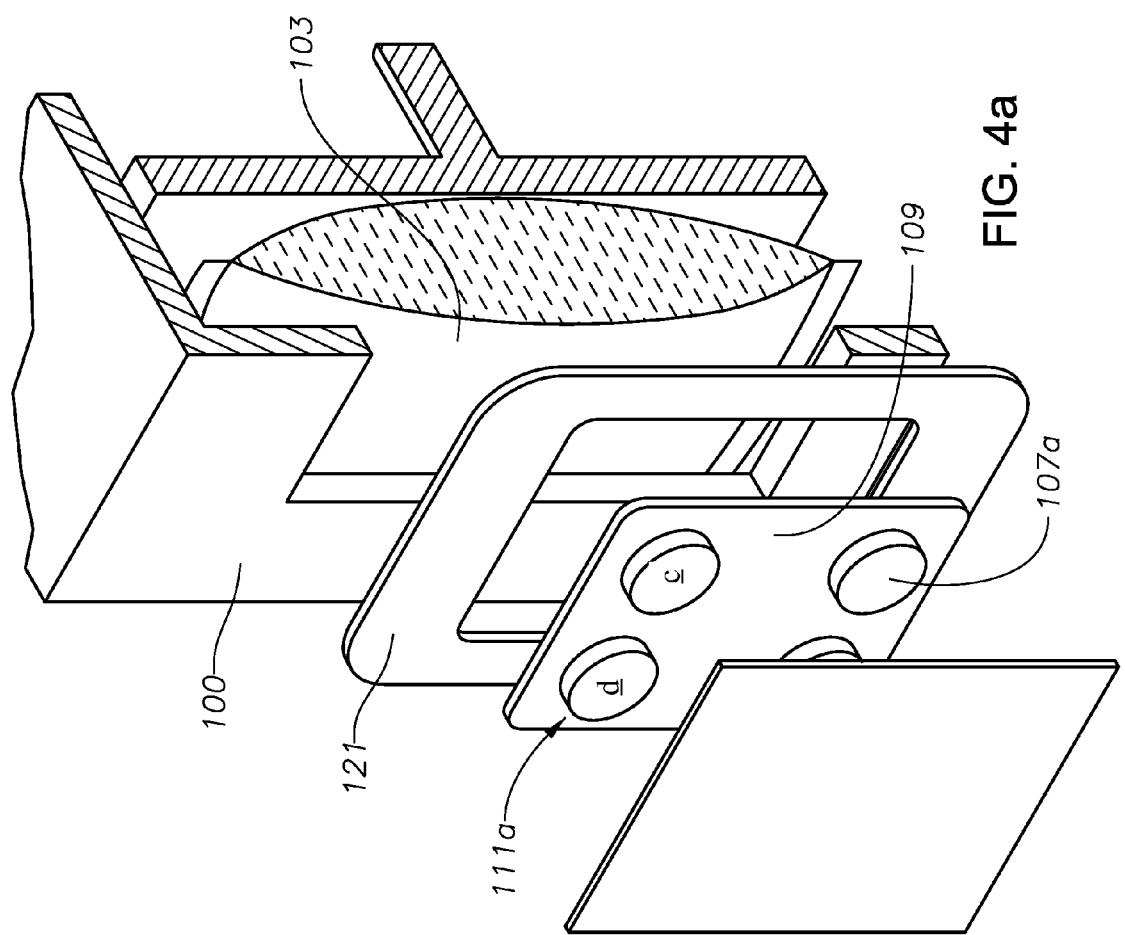
FIG. 4a
FIG. 4b

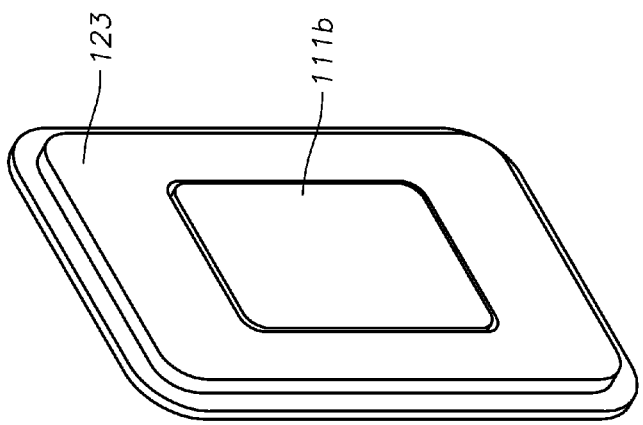
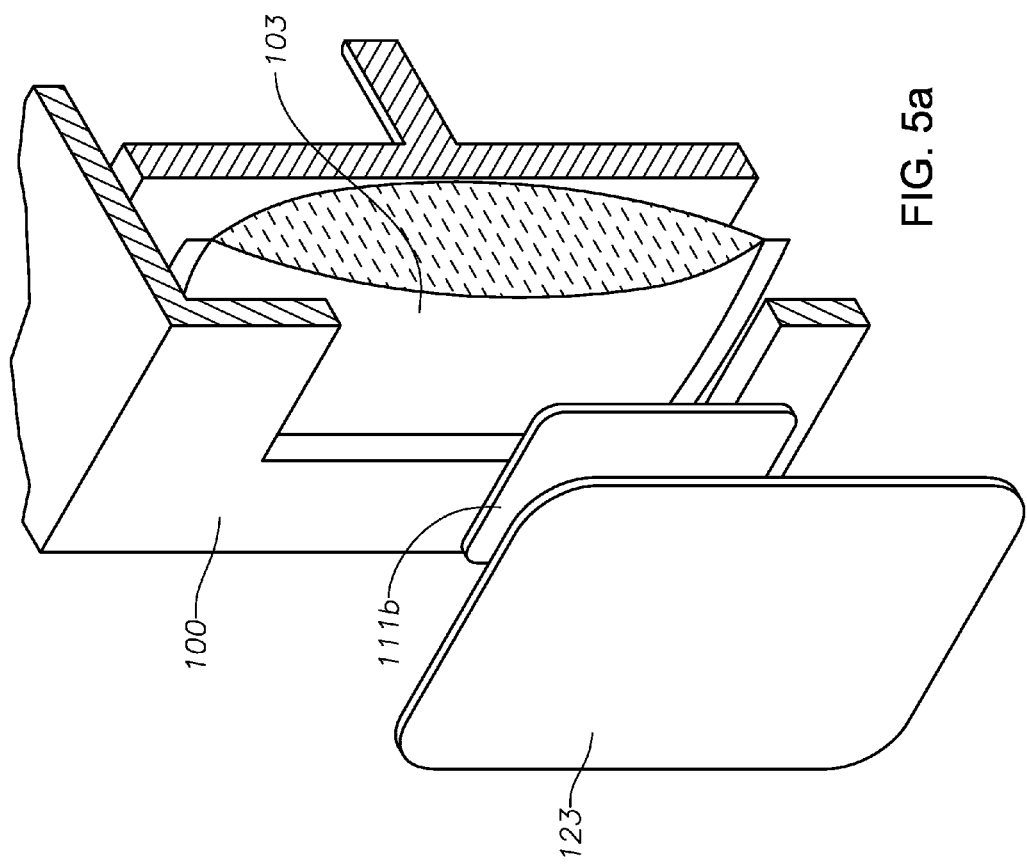
FIG. 5a
FIG. 5b

| | |
|---|---|
| The flexible container may be placed between the squeeze plate and the pressure sensor module. | 901 |
| The squeeze plate and/or the pressure sensor module may be moved to exert a pressure on the flexible container. | 903 |
| A pressure of the flexible container may be measured through the pressure sensor on the pressure sensor module. | 905 |

SYSTEMS AND METHODS FOR EXTERNAL PRESSURE SENSING

FIELD OF THE INVENTION

The present invention generally pertains to pressure detection. More particularly, but not by way of limitation, the present invention pertains to measuring pressure on an external surface of a flexible container.

DESCRIPTION OF THE RELATED ART

Surgical systems may be used to provide irrigation to a body part during surgery. For example, an ophthalmic surgical system may be used to provide irrigation to the eye during a cataract removal procedure.

SUMMARY

In various embodiments, a device for delivering pressurized irrigation may include a squeeze plate and a pressure sensor module. The squeeze plate may be configured to move relative to the pressure sensor module to apply pressure to a flexible container (e.g., a bag of irrigation fluid) between the squeeze plate and the pressure sensor module. The pressure sensor module may include a force sensor to measure a force exerted on the pressure sensor module by the flexible container as pressure is applied to the flexible container from the squeeze plate. In some embodiments, the pressure sensor module may include a bag contact plate and the force sensor may measure a force exerted on the bag contact plate by the flexible container located between the bag contact plate and the squeeze plate.

In some embodiments, the pressure sensor module may include a hinge on an end of the bag contact plate and the force sensor may be arranged to measure a force exerted on the force sensor by the bag contact plate as the bag contact plate pivots relative to the hinge when force is exerted on the bag contact plate by the flexible container located between the squeeze plate and the bag contact plate.

In some embodiments, the pressure sensor module may include more than one force sensor located on an opposing side of the bag contact plate as a side of the bag contact plate in contact with the flexible container. The output from the force sensors may be, for example, added, averaged, or compared to determine a relative force on the pressure sensor module.

In some embodiments, the force sensor may include a capacitive sensor in contact with the flexible container. In some embodiments, a capacitive sensor array (which may include more than one capacitive sensor) may be placed in contact with the flexible container (such that several areas of the flexible container are in contact with the various sensors of the capacitive sensor array).

Other force sensors are also contemplated. For example, the force sensor may include a stylus with a face configured to contact the flexible container. In some embodiments, the pressure sensor module may include a membrane and an internal load cell with a fluid separating the membrane from the internal load cell such that a force exerted on the membrane is transmitted to the internal load cell through the fluid. In some embodiments, a bag filled with a fluid may be placed between the membrane and the flexible container to distribute force from the flexible container over the membrane.

In various embodiments, a method of measuring the pressure associated with the flexible container may include placing the flexible container between the squeeze plate and the pressure sensor module, moving at least one of the squeeze plate and the pressure sensor module to exert a pressure on the flexible container, and measuring a pressure on the flexible container through the force sensor on the pressure sensor module.

BRIEF DESCRIPTION OF THE DRAWINGS

For a more complete understanding of the present invention, reference is made to the following description taken in conjunction with the accompanying drawings in which:

FIGS. 4a-b illustrate a pressure measurement system with a bag contact plate with multiple force sensors, according to an embodiment;

FIGS. 5a-b illustrate a pressure measurement system with a capacitive sensor array, according to an embodiment;

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
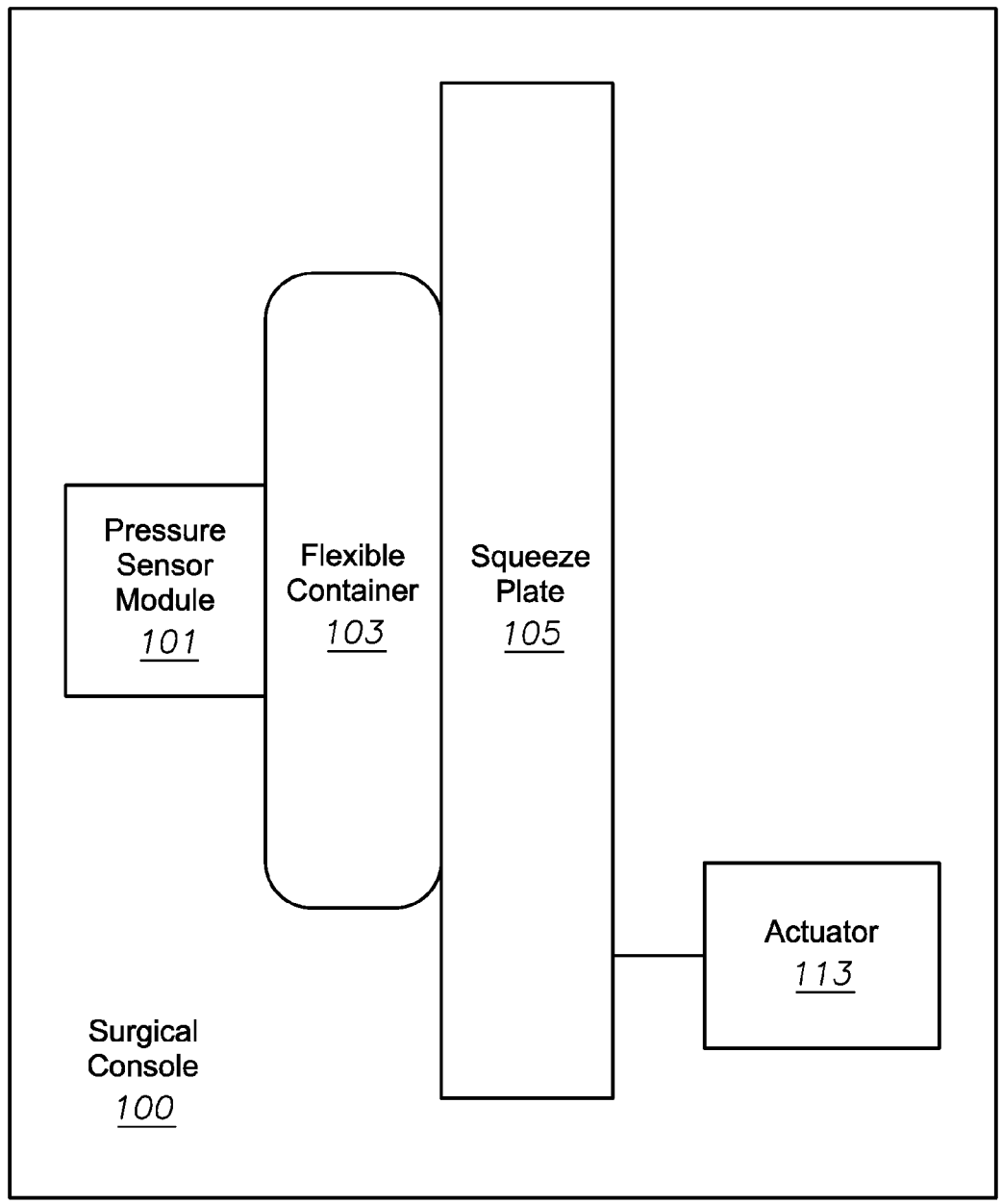
FIG. 1 illustrates a flexible container between a pressure sensor module and a squeeze plate, according to an embodiment.

FIG. 1 illustrates an embodiment of a flexible container 103 between a pressure sensor module 101 and a squeeze plate 105. In various embodiments, a surgical console 100 (e.g., an ophthalmic surgical console) may be used to deliver pressurized irrigation to a body part (such as the eye) during a surgical procedure (e.g., as described in U.S. Pat. No. 7,806,865, Ser. No. 12/469,354, by Daniel J. Wilson, filed May 20, 2009, which is hereby incorporated by reference in its entirety as though fully and completely set forth herein). In some embodiments, the pressurized system may include a squeeze plate 105 and a pressure sensor module 101. The squeeze plate 105 may be configured to move relative to the pressure sensor module 101 to apply pressure to the flexible container 103 (e.g., a bag of irrigation fluid such as BSS™ (Balanced Salt Solution)) between the squeeze plate 105 and the pressure sensor module 101. In some embodiments, the squeeze plate 105 may include a rigid material (e.g., a rigid plastic, metal, etc.) or may include a flexible material (such as the flexible band described in U.S. Pat. No. 7,806,865). The squeeze plate 105 may provide a surface that contacts at least a portion of the flexible container 103 to compress the flexible container 103. In some embodiments, a contact area between the flexible container 103 and the squeeze plate 105 may be determined and stored in the console.

In some embodiments, the squeeze plate 105 may be moved by an actuator 113 (such as an electric motor (e.g., a stepper motor), a pneumatic cylinder, an electro-magnet, etc). In some embodiments, the squeeze plate 105 may be pushed/pulled at a controlled rate using a stepper motor or an electromagnet controlled by a fluidics management system 1005 (e.g., see FIG. 10). In some embodiments, the fluidics management system may use a determined pressure of the flexible container 103 (e.g., as determined through the pressure sensor module 101) to control the movement of the squeeze plate 105. For example, the rate of squeeze plate movement may be slowed, stopped, or reversed to decrease pressure in the flexible container 103 or the rate of squeeze plate movement may be increased to increase the pressure in the flexible container 103. The rate of squeeze plate movement may also be maintained when a desired pressure of the flexible container 103 has been measured by the pressure sensor module 101.

Figure 2B:
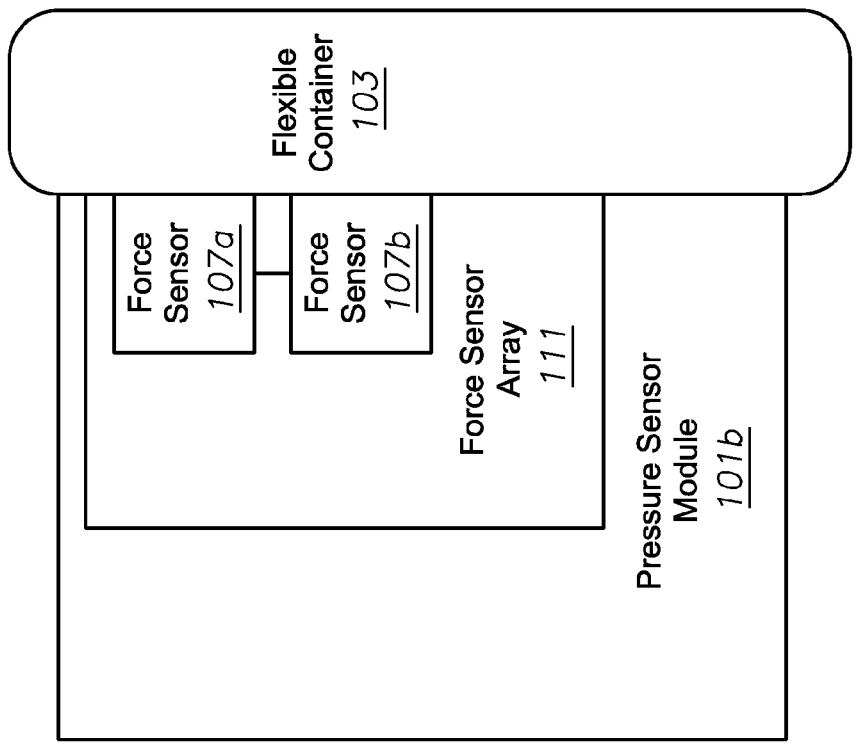
FIGS. 2a-b illustrate pressure sensor modules, according to various embodiments.
Figure 2A:
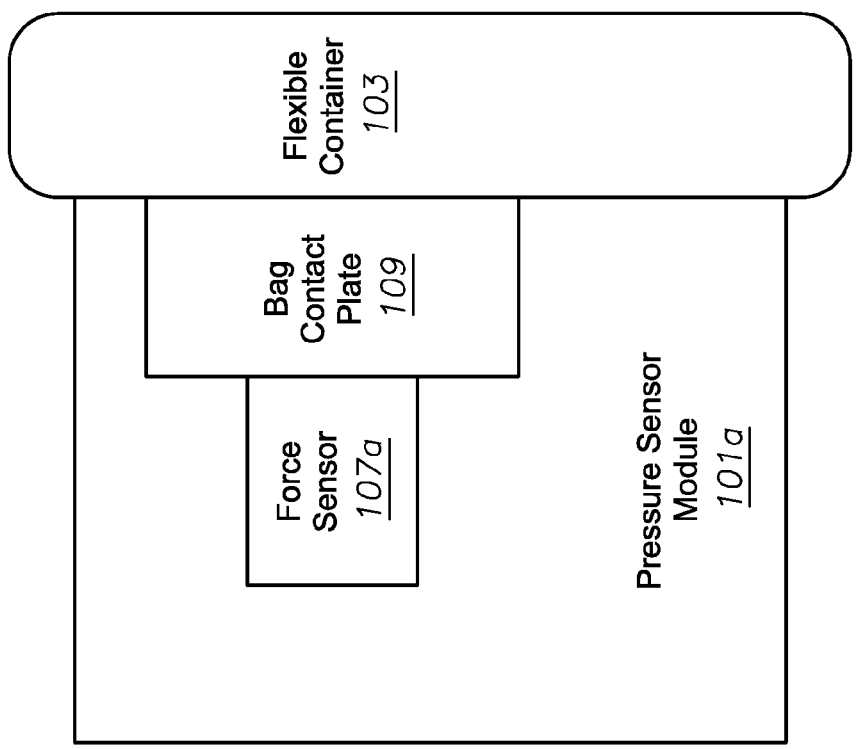

FIGS. 2a-b illustrate various embodiments of pressure sensor modules 101 (specific embodiments of the module are shown as 101a, 101b, etc. while the module is referred to generally as "101"). The pressure sensor module 101a may include one or more force sensors 107 (e.g., force sensors 107a, b, etc.) to measure a force exerted on the pressure sensor module 101a by the flexible container 103 as pressure is applied to the flexible container 103 from the squeeze plate 105. In various embodiments, the force sensors may be external to a patient fluid path (and therefore be non-invasive to the fluid system). Force sensors may include load cells (e.g., strain gauge load cells or hydraulic or pneumatic based load cells), piezoelectric crystal sensors, etc. As seen in FIG. 2a, in some embodiments, the pressure sensor module 101a may include a bag contact plate 109 and the force sensor 107a may measure a force exerted on the bag contact plate 109 by the flexible container 103 located between the bag contact plate 109 and the squeeze plate 105. By using the contact area between the flexible container 103 and the bag contact plate 109 and the force measured by the force sensor 107a, a pressure associated with the flexible container 103 may be determined (e.g., according to Pressure=Force/Area). The pressure associated with the flexible container may be a pressure that is identical to the pressure inside the flexible container, a pressure that is proportionate to a pressure inside the flexible container, or may include a pressure that has been correlated to a pressure inside the flexible container (e.g., measured pressure sensor module pressures may be recorded for known flexible container pressures (e.g., in a controlled modeling exercise) and the correlations may be used to approximate an actual flexible container pressure based on a measured pressure from the pressure sensor module during actual use). As seen in FIG. 2b, in some embodiments, the pressure sensor module 101b may not include a bag contact plate 109. In some embodiments, the pressure sensor module 101b may include one or more force sensors 107a,b in a force sensor array 111 that measures force at various points on the flexible container 103.

Figure 3:
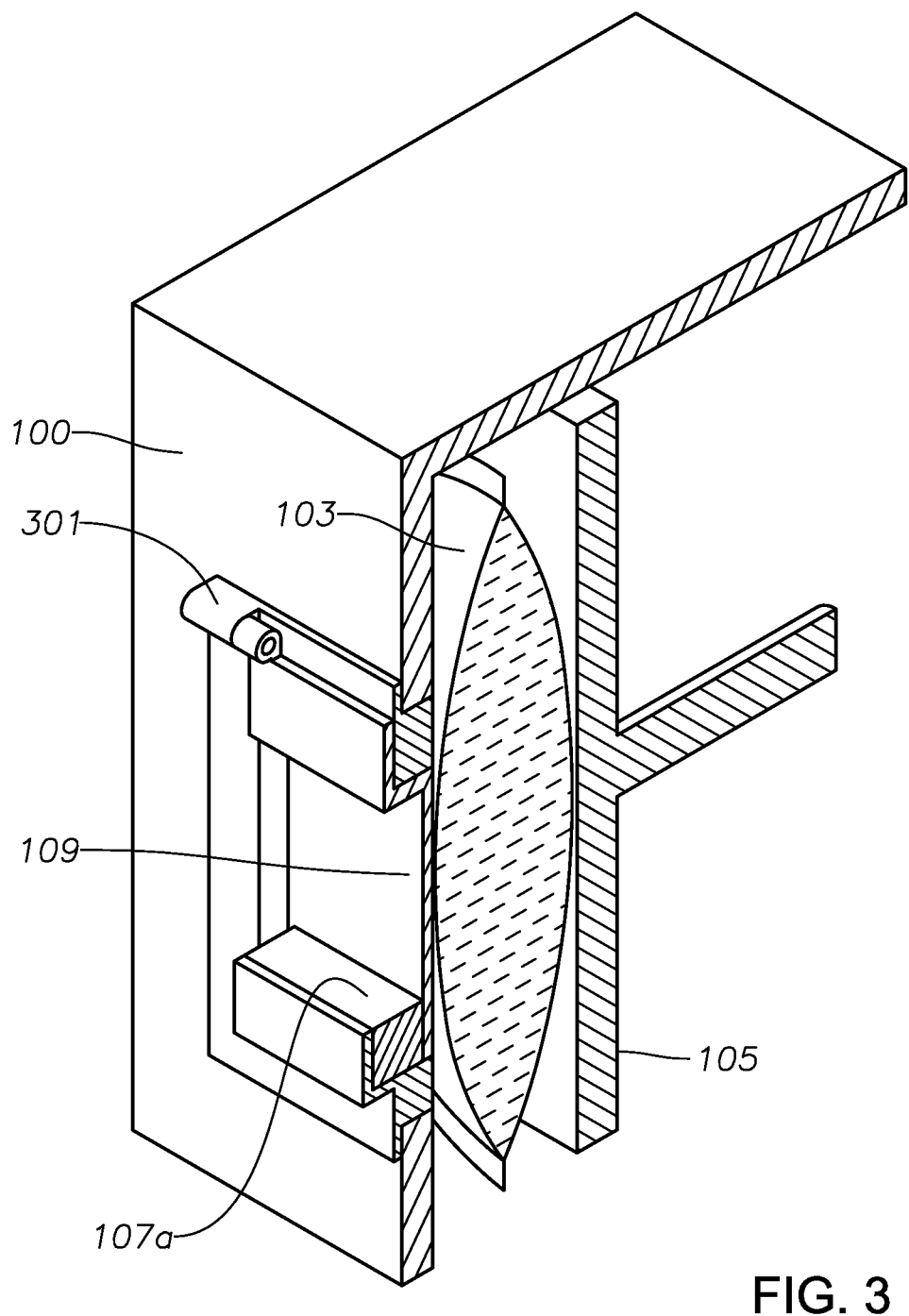
FIG. 3 illustrates a pressure measurement system with a hinged bag contact plate, according to an embodiment.

FIG. 3 is a cut-away view of an embodiment of a pressure measurement system (shown on a portion of the surgical console 100) with a hinged bag contact plate 109. In some embodiments, the pressure sensor module 101 may include a hinge 301 on an end of the bag contact plate 109 and the force sensor 107a (e.g., a load cell) may be arranged to measure a force exerted on the force sensor 107a by the bag contact plate 109 as the bag contact plate 109 pivots relative to the hinge 301 when force is exerted on the bag contact plate 109 by the flexible container 103 located between the squeeze plate 105 and the bag contact plate 109. In some embodiments, the hinge may include a fixed rod (e.g., fixed relative to the surgical console 100) through the center of a hollowed cylindrical portion of the bag contact plate 109 that allows the bag contact plate 109 to rotate relative to the fixed rod. Other hinge configurations are also contemplated. In some embodiments, the force exerted on the force sensor 107a may be attributed to an area of contact between the flexible container 103 that spans a larger area than the area of the bag contact plate 109 that is directly over the force sensor 107a (the larger area of contact between the flexible container and the bag contact plate may be accounted for in determining the pressure of the flexible container based on the measured force from force sensor 107a (e.g., pressure of flexible container=measured force from force sensor 107a multiplied by two (because half the force goes through the hinge)/area of contact between the flexible container and the bag contact plate 109)). Other calculations may also be used (e.g., the equations for pressure may vary to account for the location of the force sensor 107a relative to the hinge, the distance between the area of contact (between the flexible container and the bag contact plate) and the center of the bag contact plate, etc). In some embodiments, for example with complicated arrangements of the bag contact plate, the flexible container, and the force sensor, a flexible container pressure versus measured force may be modeled (e.g., using several known flexible container pressures and their resultant force detections to form an equation (or chart) relating the measured force to the flexible container pressure).

FIGS. 4a-b illustrate an embodiment of a pressure measurement system (shown on a portion of the surgical console 100) with a bag contact plate 109 having a force sensor array 111a (e.g., including multiple force sensors 107a-d). In some embodiments, a mounting plate 121 may be used to mount the bag contact plate 109 to the surgical console 100. In some embodiments, the pressure sensor module 101 may include more than one force sensor 107 located on an opposing side of the bag contact plate 109 as a side of the bag contact plate 109 in contact with the flexible container 103. The output from the force sensors 107a-d on the sensor array 111a may be, for example, added, averaged, or compared to determine a relative force on the pressure sensor module 101. In some embodiments, the measured force on each sensor 107 may be added together and the total may be divided by the area of the bag contact plate 109 to determine pressure of the flexible container. As noted above, in some embodiments, an equation (or chart) relating measured force and the corresponding pressure inside the flexible container may be modeled (based on known pressures and their resultant measured forces).

FIGS. 5a-b illustrate an embodiment of a pressure measurement system (shown on a portion of the surgical console 100) with a force sensor array 111b (e.g., including a capacitive sensor array). In some embodiments, the force sensor 107 may include one or more capacitive sensors in an array 111b arranged to contact the flexible container 103. Other sensor types are also contemplated (e.g., conductive polymer). In some embodiments, the capacitive sensor array 111b may be placed in contact with the flexible container 103 (such that several areas of the flexible container 103 are in contact with the various sensors 107 of the capacitive sensor array 111b). In some embodiments, a mounting plate 123 may be used to mount the array 111b to the surgical console 100. The output from the capacitive sensors on the capacitive sensor array 111b may be, for example, added, averaged, or compared to determine a relative force on the pressure sensor module 101. In some embodiments, the measured force on the capacitive sensors may be added together and the total may be divided by the area of the bag contact plate 109 to determine pressure of the flexible container. As noted above, in some embodiments, an equation (or chart) relating measured force and the corresponding pressure inside the flexible container may be modeled (based on known pressures and their resultant measured forces). Other force sensors 107 and force sensor arrangements are also contemplated.

Figure 6A:
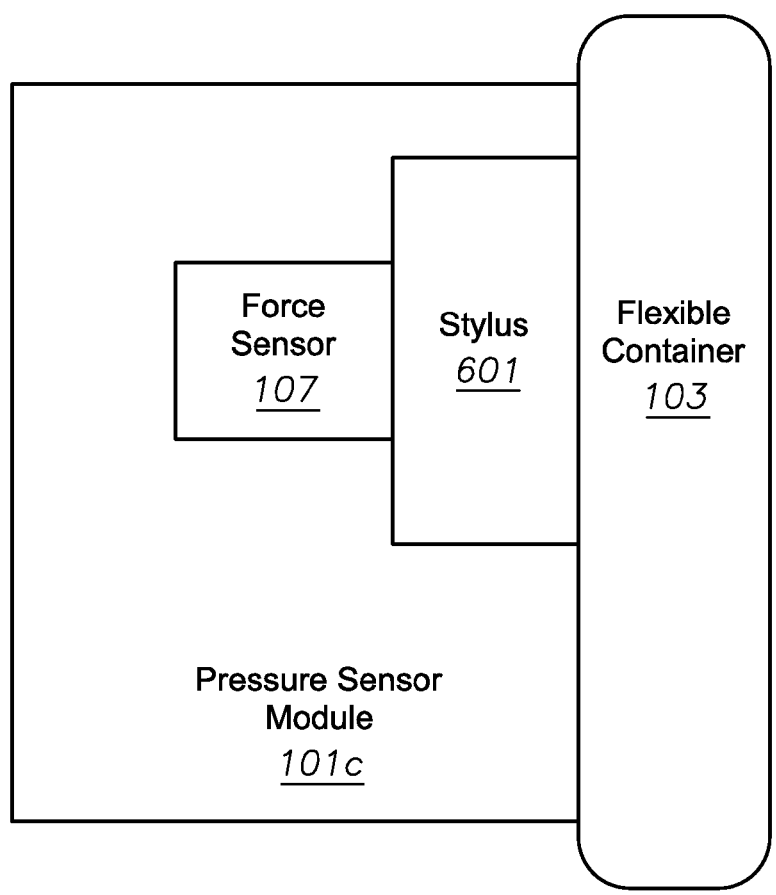
FIGS. 6a-b illustrate a pressure measurement system with a load cell using a stylus in contact with the flexible container, according to an embodiment.
Figure 6B:
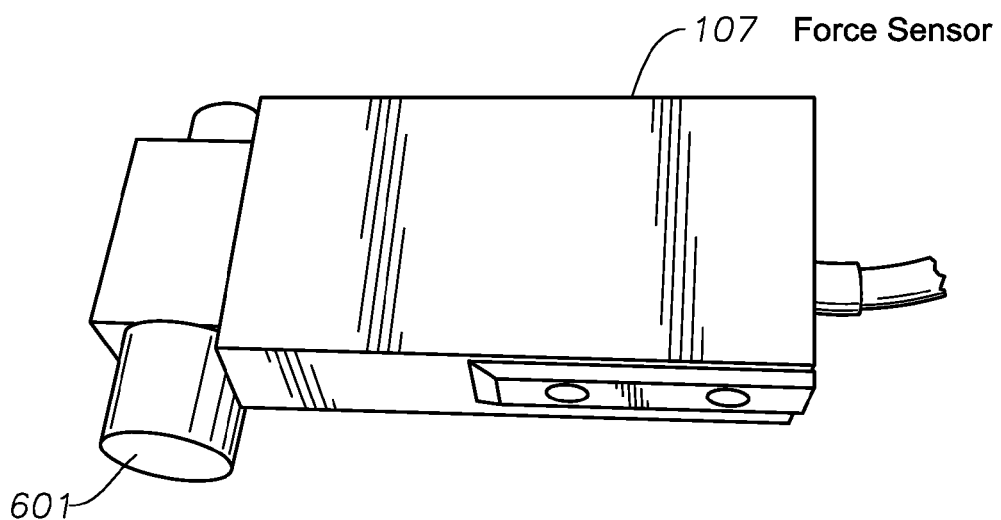

In some embodiments, as seen in FIGS. 6a-b, the pressure sensor module 101c may include a force sensor 107 with a stylus 601 having a face configured to contact the flexible container 103. The stylus 601 may be a biased, mechanically movable object (e.g., a lever, a button, a reed, etc.) that moves in response to a force. The degree of motion may be proportional to the acting force. The stylus 601 may be exposed (e.g., a reed or lever in direct contact with the flexible container 103) or may be covered by a flexible covering (such as a membrane) that protects the stylus 601 but transmits an external force (e.g., from the flexible container 103 to the stylus). In some embodiments, the stylus may include a flexible covering with a flexible round flat face of approximately 0.5 inch diameter. Other diameters and shapes are also contemplated (e.g., approximately in a range of 0.1 to 1 inch in diameter, approximately in a range of 1 inch to 5 inches in diameter, etc). In some embodiments, the bag pressure may be proportional to the force output on the stylus or covering (which may be at least partially dependent on the stylus area (or area of the flexible covering in contact with the stylus)). As noted above, in some embodiments, the pressure may be determined through modeling by determining the force measured through the force sensor 107 and comparing it to the actual pressure of the bag (which may be known in the modeling scenario). An equation or chart may be developed to use in actual use to determine the bag pressure using the actual measured force on the stylus or covering.

Figure 7A:
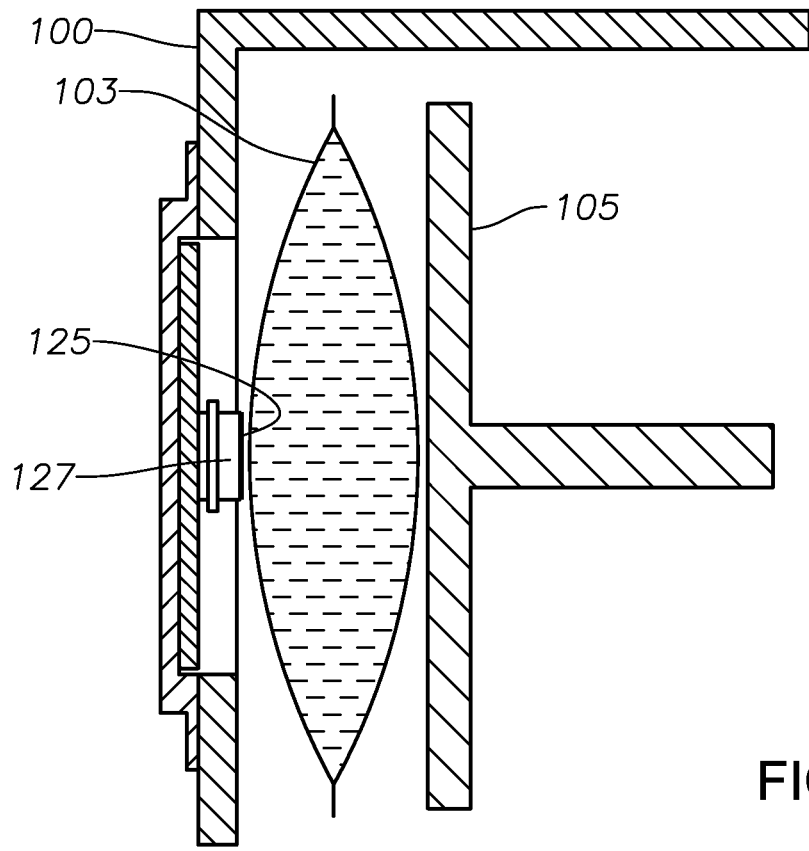
FIGS. 7a-b illustrate a pressure measurement system with a pressure transducer having a membrane, according to an embodiment.
Figure 7B:
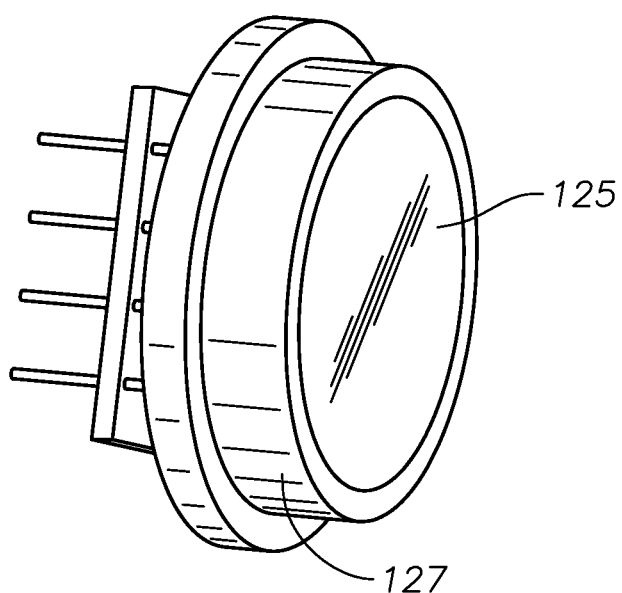

As seen in FIGS. 7a-b, the pressure sensor module 101 may include a membrane 125 and a load cell 127. The pressure sensor module 101 may include a fluid (such as liquid (e.g., water or oil), gel, air, etc.) separating the membrane 125 from an internal load cell such that a force exerted on the membrane 125 is distributed over the internal load cell through the fluid. In some embodiments, the load cells may include a strain gauge or may be hydraulic or pneumatic based (other load cell types are also contemplated).

Figures 8, 9:
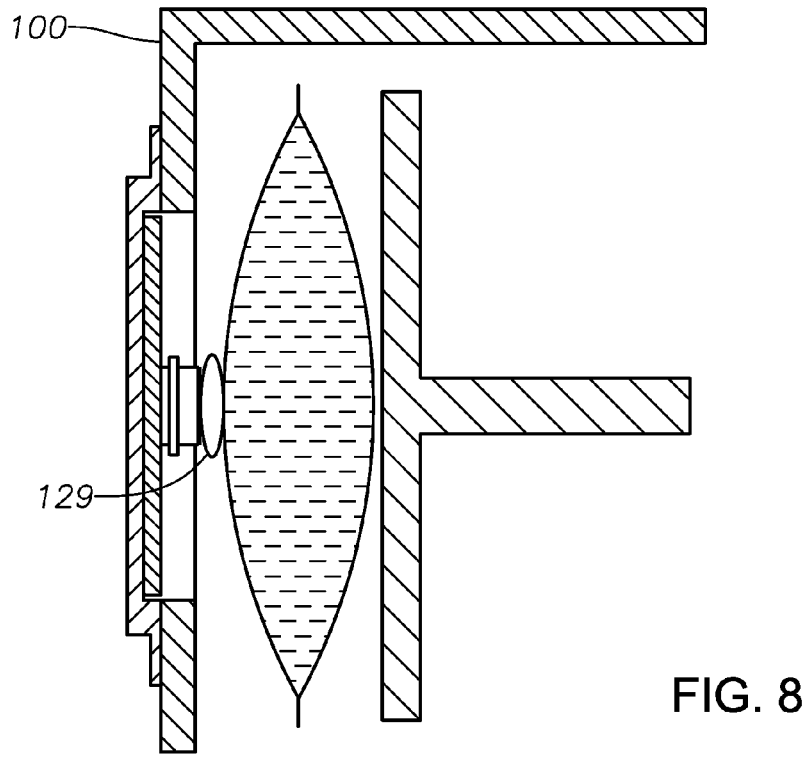
FIG. 8 illustrates a pressure measurement system with an additional pressure distributing bag between the pressure transducer membrane and the flexible container, according to an embodiment.
FIG. 9 illustrates a flowchart of a method for measuring a pressure associated with a flexible container, according to an embodiment.

As seen in FIG. 8, a bag 129 filled with a fluid may be placed between the membrane 125 and the flexible container to distribute pressure from the flexible container over the membrane 125. For example, if the flexible container 103 had uneven pressure spots (such as wrinkles on the surface), the bag 129 may distribute the force from the uneven spot over the load cell (instead of, for example, part or all of a wrinkle in the flexible container pressing against the sensor and providing a locally inaccurate reading). The bag may be filled with a liquid (e.g., water or oil), gel, air, etc. The bag may be coupled to the membrane 125 (e.g., through an adhesive) or may be loosely held next to the membrane 125.

FIG. 9 illustrates a method of measuring the pressure associated with the flexible container 103. The elements provided in the flowchart are illustrative only. Various provided elements may be omitted, additional elements may be added, and/or various elements may be performed in a different order than provided below.

At 901, the flexible container 103 may be placed between the squeeze plate 105 and the pressure sensor module 101. For example, a bag of BSS™ solution may suspended (e.g., by the neck as seen in FIG. 3) between the squeeze plate 105 and the pressure sensor module 101. In some embodiments, the flexible container may be laid horizontal between the squeeze plate 105 and the pressure sensor module 101. Other orientations and coupling configurations are also contemplated.

At 903, at least one of the squeeze plate 105 and the pressure sensor module 101 may be moved relative to the other of the squeeze plate 105 and the pressure sensor module 101 to exert a pressure on the flexible container 103. For example, a displacement motor may push a rigid squeeze plate 105 to reduce a space between the squeeze plate 105 and the pressure sensor module 101. As another example, the squeeze plate 105 may be a flexible band that may be pulled (e.g., see U.S. Pat. No. 7,806,865) to squeeze a flexible container 103 between the squeeze plate 105 and the pressure sensor module 101.

At 905, a pressure of the flexible container 103 may be measured through the force sensors on the pressure sensor module 101. The force/pressure sensors may measure a force from the surface of the flexible container 103 to determine an internal pressure of the flexible container 103.

Figure 10:
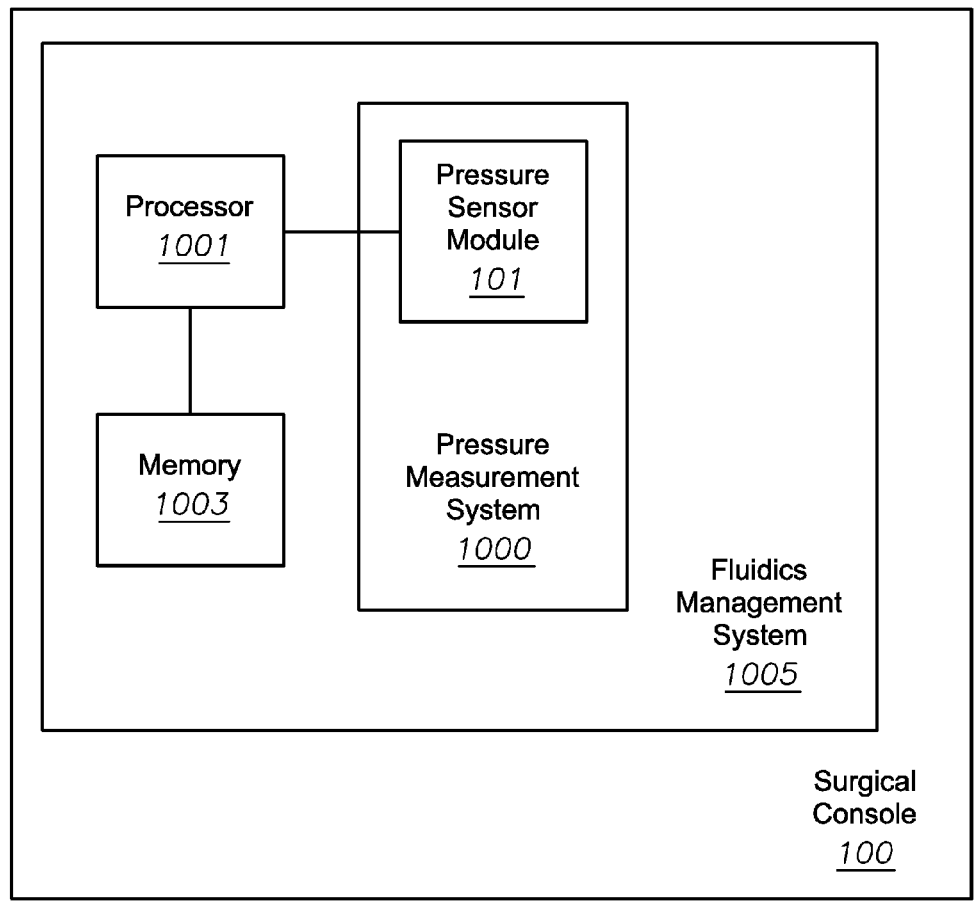
FIG. 10 illustrates a pressure measurement system, according to an embodiment.

As seen in FIG. 10, in some embodiments, the pressure measurement system 1000 may include or be coupled to one or more processors (e.g., processor 1001). The processor 1001 may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory 1003 coupled to and/or embedded in the processors 1001 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors 1001 implement one or more of its functions via a state machine, analog circuitry, digital circuitry, and/or logic circuitry, the memory 1003 storing the corresponding operational instructions may be embedded within, or external to, the circuitry comprising the state machine, analog circuitry, digital circuitry, and/or logic circuitry. The memory 1003 may store, and the processor 1001 may execute, operational instructions corresponding to at least some of the elements illustrated and described in association with the figures.

Figure 11:
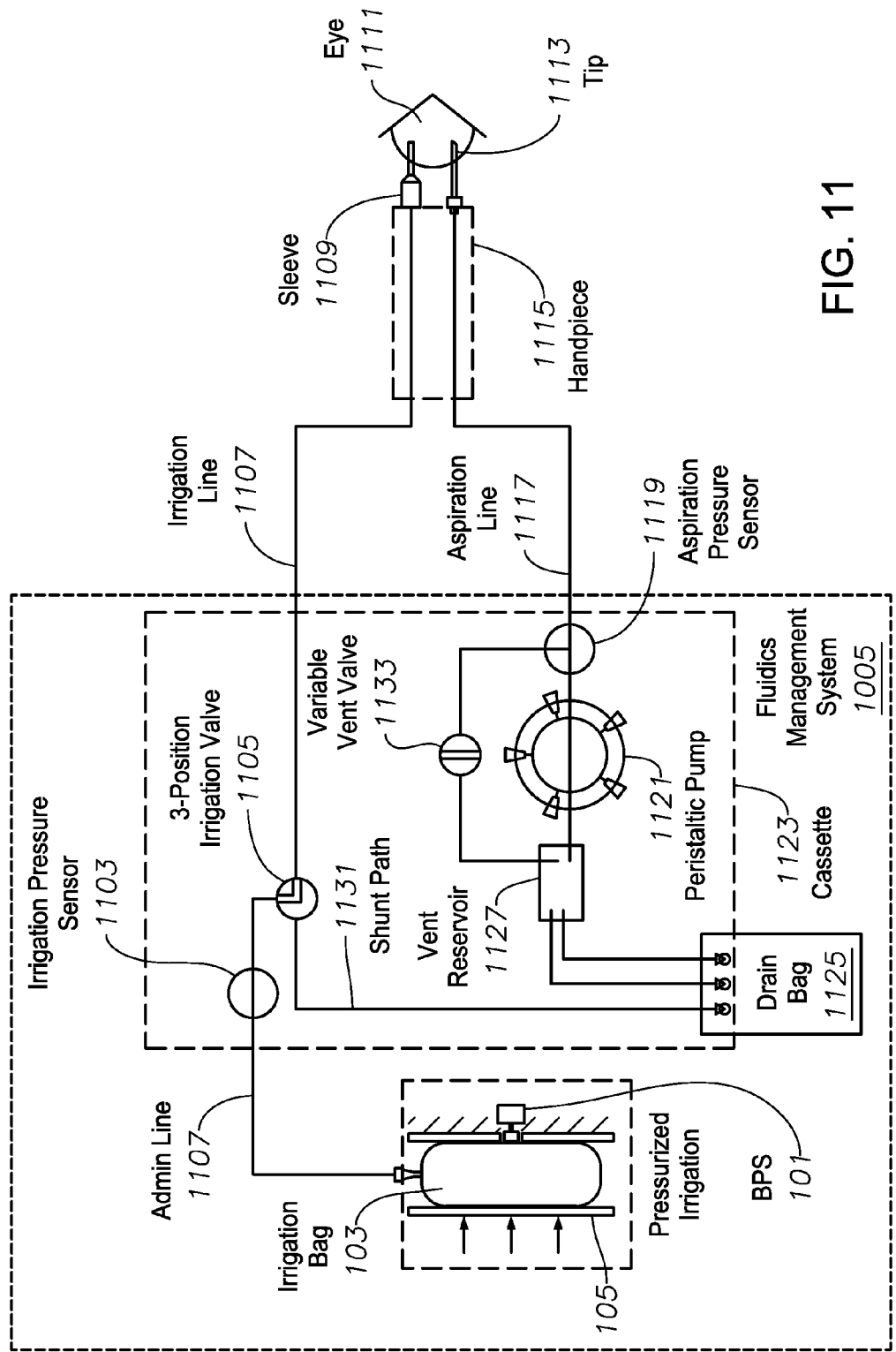
FIG. 11 illustrates a fluidics management system incorporating the pressure sensor module.

FIG. 11 illustrates a fluidics management system 1005 incorporating the pressure sensor module 101. In some embodiments, the fluidics management system 1005 may include a pressurized irrigation system that includes a squeeze plate 105 applying pressure to a flexible container 103 (such as a BSS™ irrigation bag) and a pressure sensor module 101 to measure an external pressure on the outside of the flexible container 103. Irrigation fluid from the flexible container 103 may flow through an administration line 1107, an irrigation pressure sensor 1103, an irrigation valve 1105 (e.g., a 3 position irrigation valve), an irrigation line 1107, a handpiece 1115, through a sleeve 1109, and into the eye 1111. In some embodiments, the fluidics management system 1005 may use a pressure from the pressure sensor module 101 instead of or in addition to a separate irrigation pressure sensor on the irrigation line 1107. For example, the pressure sensor module 101 may provide a redundant or fail-safe pressure sensor that can be used to stop or limit the speed of the squeeze plate 105 if the pressure sensor module 101 measures a pressure on the flexible container 103 that is above a predetermined maximum pressure. In some embodiments, the system irrigation pressure (e.g., the pressure of the irrigation fluid in the irrigation line and/or entering the patient's eye from an irrigation pathway in the handpiece) may be determined using the measured pressure from the pressure sensor module 101. The measured pressure may be used to control an active stepper motor control system to move the squeeze plate to obtain and maintain a desired bag pressure (which may correspond to the system irrigation pressure). Other uses for the pressure from the pressure sensor module 101 are also contemplated (e.g., to determine when the bag is empty or near empty, to determine if a bag is present, to confirm the irrigation pressure sensor reading, etc).

In some embodiments, the pressure sensor module 101 may be used to determine the flow rate of the irrigation solution. For example, pressures from the pressure sensor module 101 may be correlated with various flow rates and stored in the system (e.g., in memory 1003) such that when a pressure is measured during operation, the corresponding flow rate can be retrieved and used by the fluidics management system 1005. Fluid may return to the fluidics management system 1005 by being aspirated through the tip 1113, into the handpiece 1115, through the aspiration line 1117 and into cassette 1123. The aspirated fluid may flow through an aspiration pressure sensor 1119, into a peristaltic pump 1121 (providing the suction for the aspiration), into a vent reservoir 1127 and into a drain bag 1125. The fluid may flow through the variable vent valve 1133 if the variable vent valve is open (e.g., during a venting or purging event). In some embodiments, irrigation fluid may flow through a shunt path 1131 from the irrigation valve 1105 (e.g., during a purge operation).

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A surgical console, comprising:
   a squeeze plate; and
   a pressure sensor module comprising a force sensor;
   wherein the squeeze plate is configured to move relative to the pressure sensor module; and
   wherein the pressure sensor module is configured to measure a force exerted on the pressure sensor module by a flexible container between the pressure sensor module and the squeeze plate, wherein the force is used to determine a pressure associated with the flexible container;
   wherein the pressure sensor module comprises a bag contact plate with a first side that is in contact with the flexible container and a second side that is on an opposing side of the bag contact plate as the first side;
   wherein the force sensor measures a force exerted on the force sensor by the second side of the bag contact plate, wherein the force from the bag contact plate is from contact with the flexible container located between the first side of the bag contact plate and the squeeze plate.

2. The surgical console of claim 1, wherein a pressure associated with the flexible container is determined using at least the measured force and a size of a contact area between the flexible container and the bag contact plate.

3. The surgical console of claim 1,
   wherein the pressure sensor module further comprises a hinge on an end of the bag contact plate between the first side and the second side; and
   wherein the force sensor is arranged to measure a force exerted on the force sensor by the bag contact plate as the bag contact plate pivots relative to the hinge as force is exerted on the bag contact plate by the flexible container located between the squeeze plate and the bag contact plate.

4. The surgical console of claim 1, wherein the pressure sensor module comprises at least one additional force sensor to measure the force exerted on the additional force sensor by the second side of the bag contact plate.

5. The surgical console of claim 1, wherein the force sensor comprises a capacitive sensor.

6. The surgical console of claim 1, wherein the force sensor is fixed relative to the squeeze plate and the bag contact plate.

7. A method, comprising:
   placing a flexible container between a squeeze plate and a pressure sensor module;
   moving at least one of the squeeze plate and the pressure sensor module to exert a pressure on the flexible container; and
   measuring a pressure associated with the flexible container through the pressure sensor module;
   wherein the pressure sensor module comprises a bag contact plate with a first side that is in contact with the flexible container and a second side that is on an opposing side of the bag contact plate as the first side;
   wherein measuring a pressure associated with the flexible container through the pressure sensor module comprises at least one force sensor on the pressure sensor module measuring a force exerted on the at least one force sensor by the second side of the bag contact plate, wherein the force from the bag contact plate is from contact with the flexible container located between the first side of the bag contact plate and the squeeze plate.

8. The method of claim 7,
   wherein the pressure sensor module further comprises a hinge on an end of the bag contact plate between the first side and the second side.

9. The method of claim 7,
   wherein measuring a pressure associated with the flexible container through the pressure sensor module comprises the pressure sensor module measuring a cumulative force on a plurality of force sensors located on the pressure sensor module;
   wherein the pressure associated with the flexible container is determined using the cumulative force measured by the plurality of force sensors and a size of a contact area between the flexible container and the bag contact plate.

10. The method of claim 7, wherein measuring a pressure associated with the flexible container through the pressure sensor module comprises at least one capacitive sensor on the pressure sensor module measuring a pressure through contact with the flexible container.

11. The method of claim 7, wherein measuring a pressure associated with the flexible container through the pressure sensor module comprises a capacitive sensor array measuring force from the flexible container along several contact points with the flexible container.

12. A surgical system, comprising:
    a squeeze plate;

pressure sensor module comprising a force sensor, wherein the squeeze plate is configured to compress an irrigation bag between the squeeze plate and the pressure sensor module;

an irrigation line configured to be coupled to a handpiece such that fluid from the irrigation bag flows through the irrigation line and into the handpiece;

wherein the pressure sensor module is configured to measure a force exerted on the pressure sensor module by a flexible container between the pressure sensor module and the squeeze plate, wherein the force is used to determine a pressure associated with the flexible container;

wherein the pressure sensor module comprises a bag contact plate with a first side that is in contact with the flexible container and a second side that is on an opposing side of the bag contact plate as the first side;

wherein the force sensor measures a force exerted on the force sensor by the second side of the bag contact plate, wherein the force from the bag contact plate is from contact with the flexible container located between the first side of the bag contact plate and the squeeze plate;

wherein the surgical system is configured to compare the pressure measured by the pressure sensor module to a predetermined maximum pressure to control movement of the squeeze plate to control the flow of irrigation fluid from the flexible container and into the irrigation line.

13. The surgical system of claim 12, further comprising a separate irrigation pressure sensor coupled to the irrigation line and wherein the surgical system compares the pressure measured by the pressure sensor module to a pressure measured by the separate irrigation pressure sensor.

14. The surgical system of claim 12, wherein the force sensor is fixed relative to the squeeze plate and the bag contact plate.

* * * * *